United States Patent [19]
Forber

[11] Patent Number: 5,984,944
[45] Date of Patent: Nov. 16, 1999

[54] INTRODUCER FOR AN EXPANDABLE VASCULAR OCCLUSION DEVICE

[75] Inventor: Simon J. Forber, Yversay, France

[73] Assignee: B. Braun Medical, Inc., Bethlehem, Pa.

[21] Appl. No.: 09/027,286

[22] Filed: Feb. 20, 1998

Related U.S. Application Data

[63] Continuation-in-part of application No. 08/927,535, Sep. 12, 1997, Pat. No. 5,895,410.

[51] Int. Cl.$^6$ .................................................. A61B 17/00
[52] U.S. Cl. .............................................................. 606/191
[58] Field of Search .................................... 606/200, 191, 606/192, 198, 108, 194; 604/104

[56] References Cited

U.S. PATENT DOCUMENTS

| | | |
|---|---|---|
| 4,592,347 | 6/1986 | Mahruki . |
| 4,732,152 | 3/1988 | Wallsten et al. .......................... 606/191 |
| 4,994,069 | 2/1991 | Ritchart et al. .......................... 606/191 |
| 5,011,488 | 4/1991 | Ginsburg .................................. 606/159 |
| 5,226,911 | 7/1993 | Chee et al. . |
| 5,250,071 | 10/1993 | Palermo ................................... 606/198 |
| 5,312,415 | 5/1994 | Palermo ................................... 606/191 |
| 5,370,134 | 12/1994 | Chin et al. ............................... 606/191 |
| 5,601,600 | 2/1997 | Ton ........................................ 606/206 |
| 5,733,294 | 3/1998 | Forber et al. . |

FOREIGN PATENT DOCUMENTS

| | | |
|---|---|---|
| 2 645 028 | 10/1990 | France . |
| 9406502 | 3/1994 | WIPO . |
| 9701368 | 1/1997 | WIPO . |

*Primary Examiner*—Michael Buiz
*Assistant Examiner*—Vikki Trinh
*Attorney, Agent, or Firm*—Skinner and Associates

[57] ABSTRACT

An introducer for introducing an expandable implantable device into a catheter includes an outer tube and an inner core which slides in the outer tube. A first end of the core has a tubular configuration with a slit which allows it to expand radially to grip an end of the device. The first end of the core holding the device is pulled into a first end of the outer tube which further tightens the grip on the device. The second end of the core, which extends beyond the second end of the outer tube, may have a handle attached or be bent to prevent the core from moving and releasing the device. The core preferably has a metal wire inside of it. The device remains in its relaxed condition attached to the introducer at the first end of the outer tube and mostly outside of it until use. The outer tube may have a rigid transparent cup-shaped shield member attached at its first end and extending beyond it to protect the device and allow the device to be viewed on the introducer. To use the introducer and the device, the core is slid relative to the outer tube which pulls the device inside the outer tube and into its stretched condition. As the first end of the inner core exits the second end of the outer tube, the end of the device is released and remains mostly inside of the outer tube in its stretched condition. An end of the outer tube is then inserted into a catheter and a pushrod used to push the device from the introducer into the catheter.

34 Claims, 14 Drawing Sheets

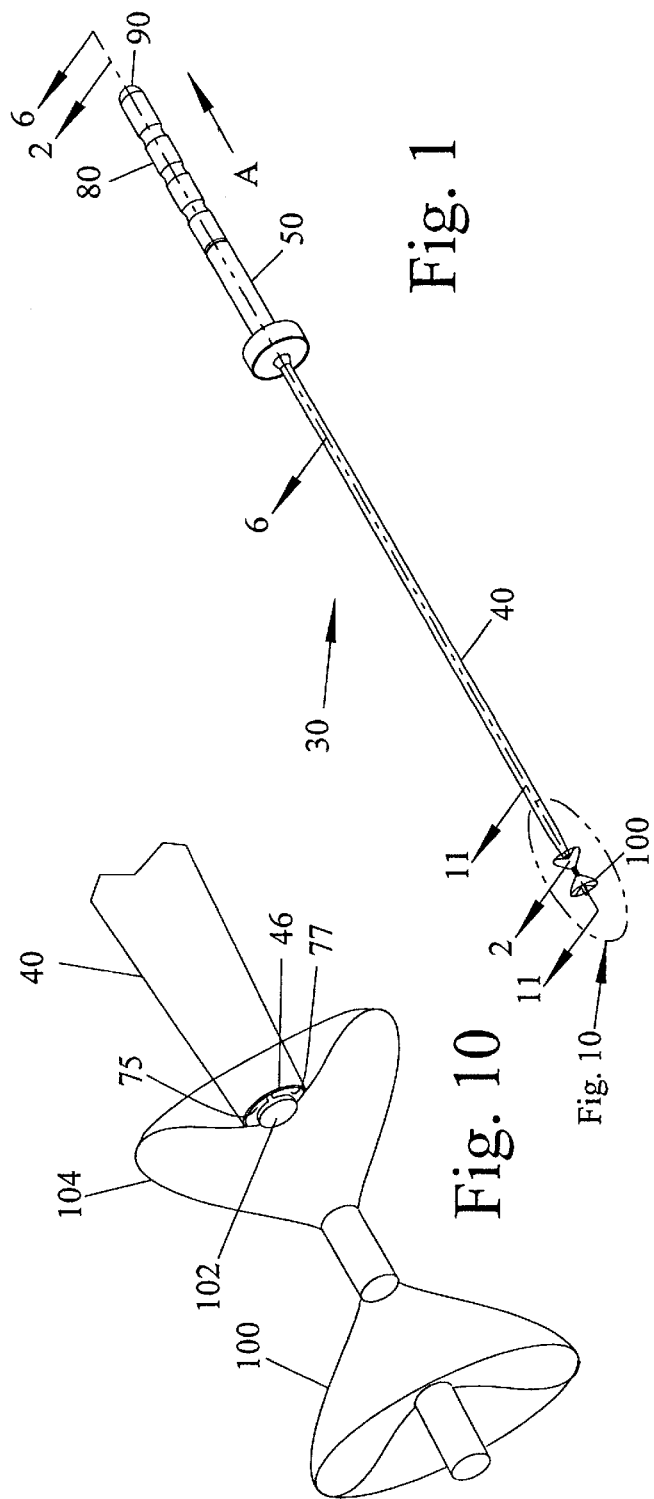

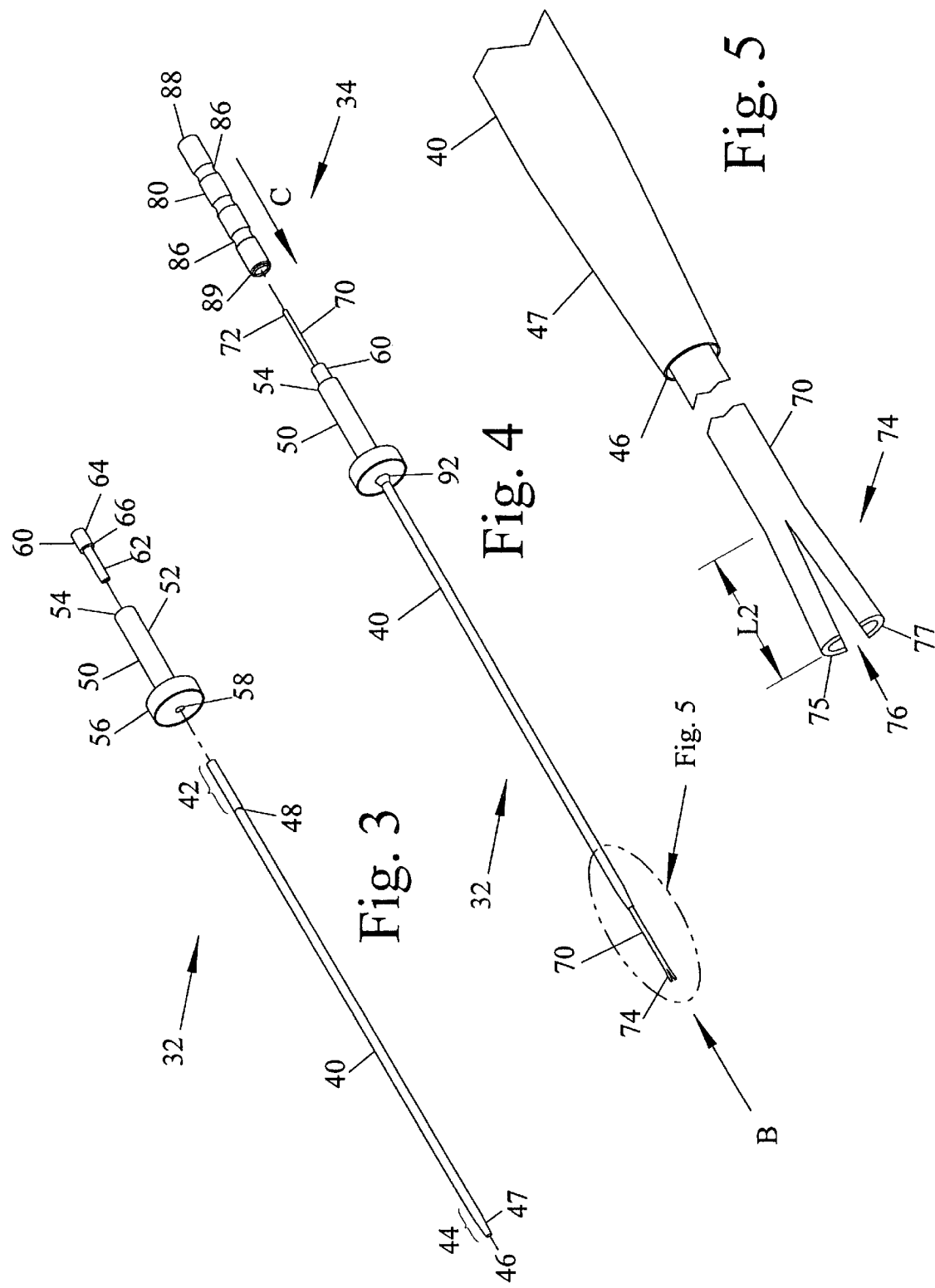

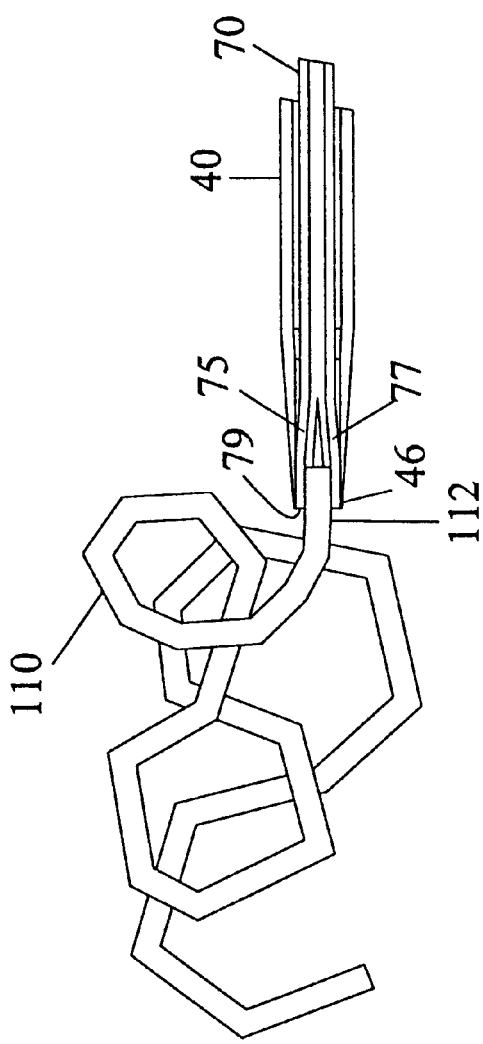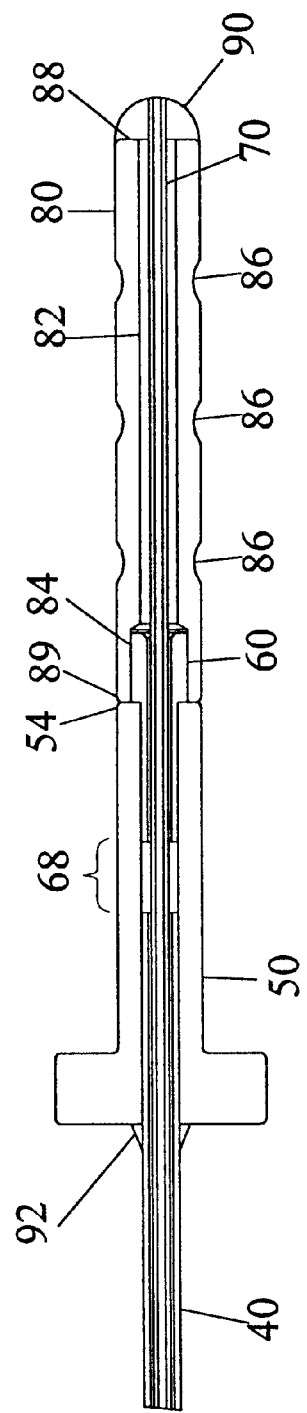

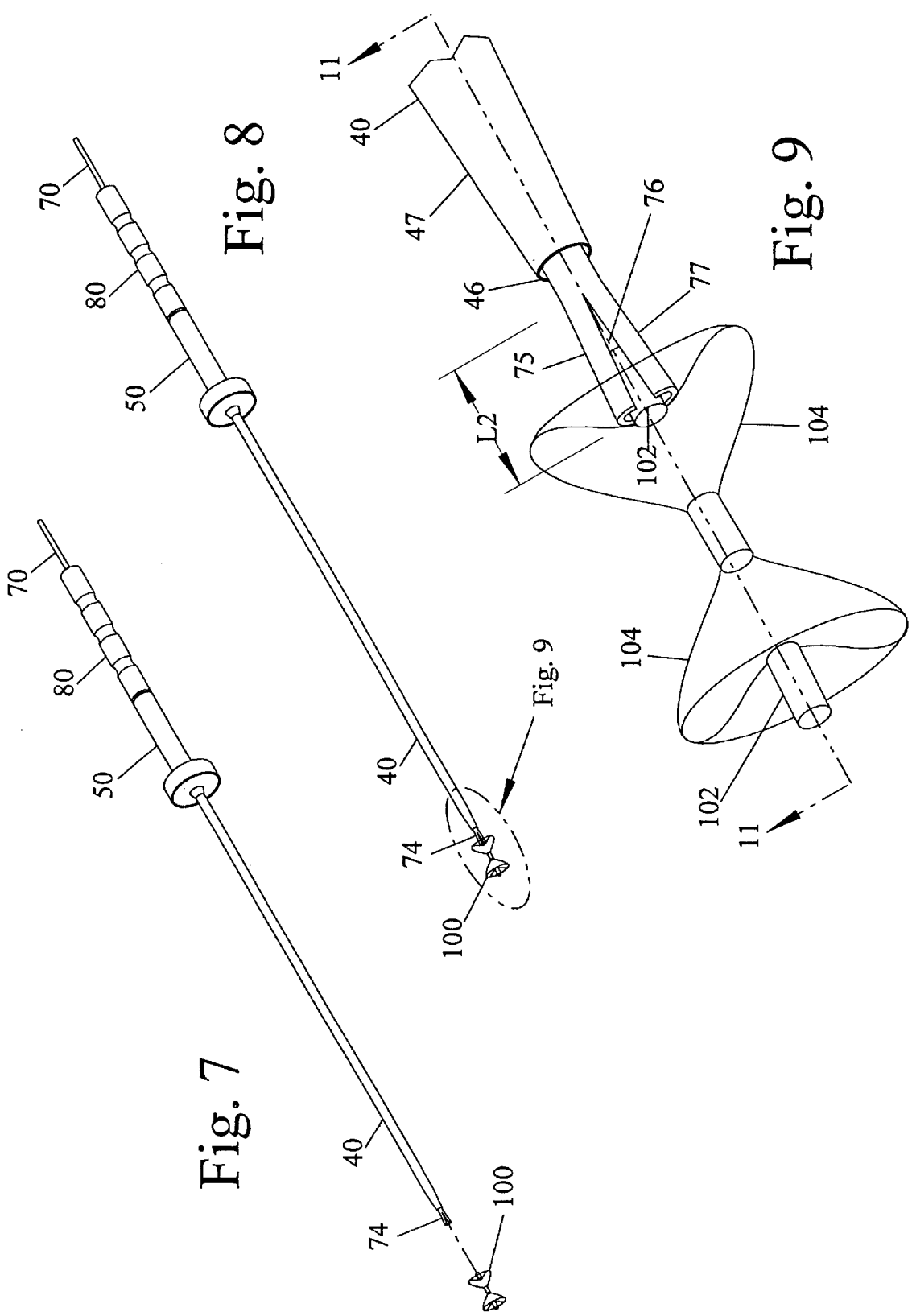

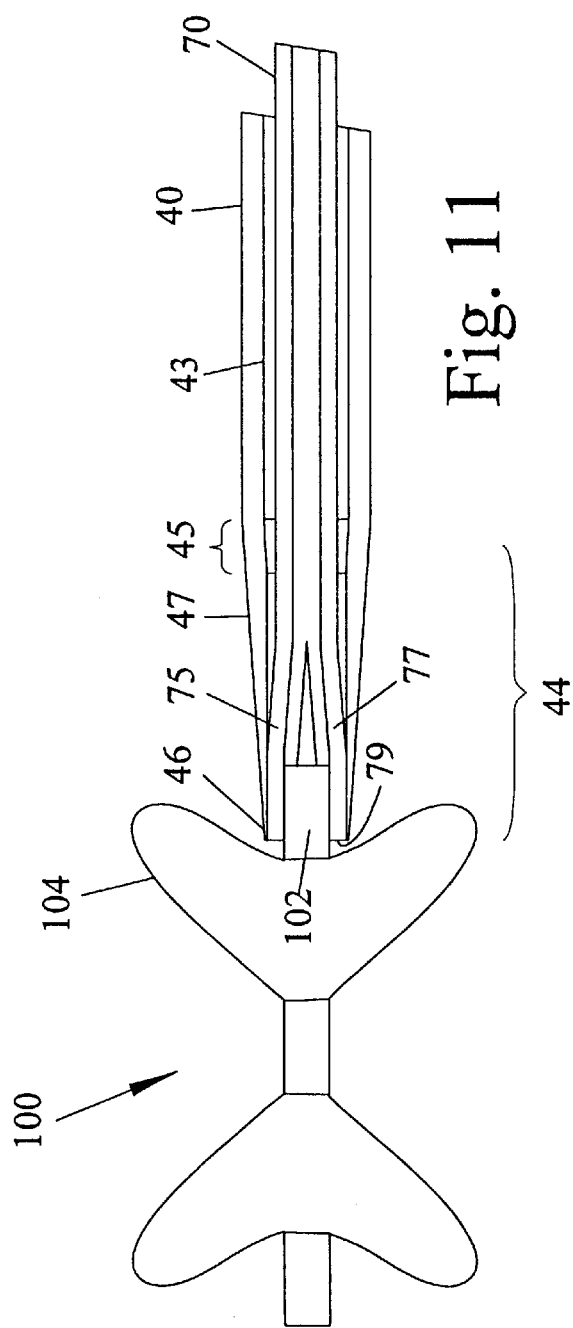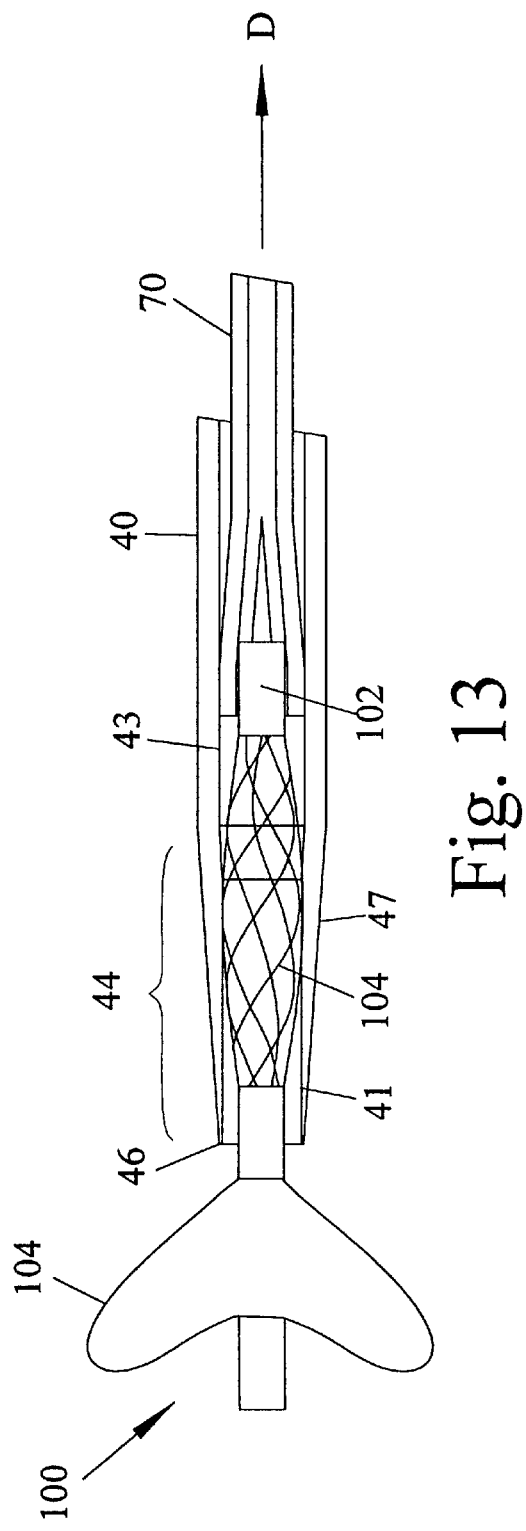

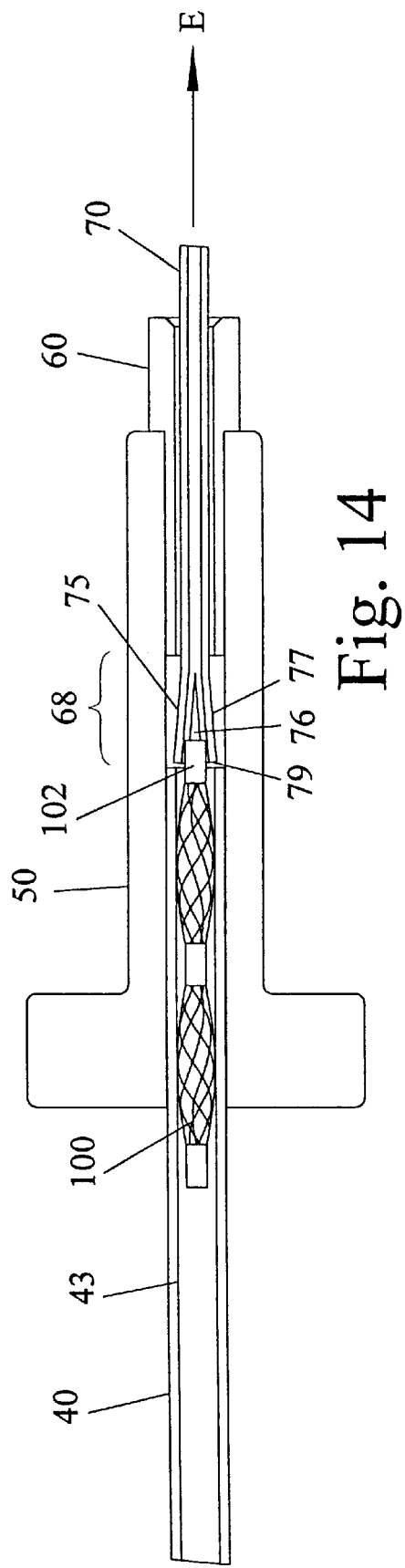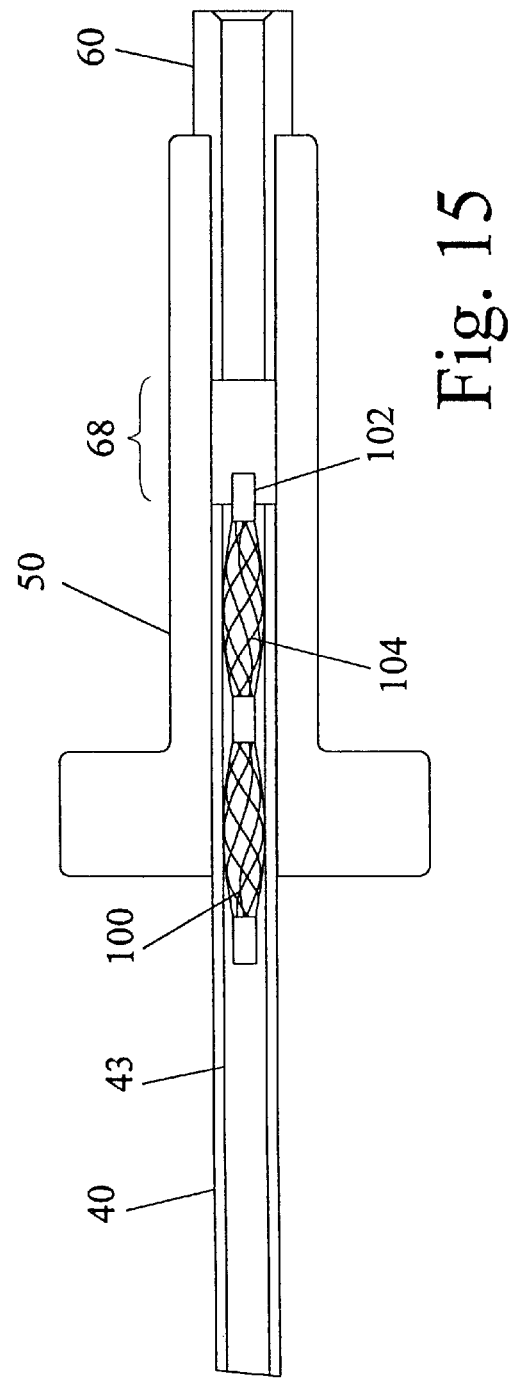

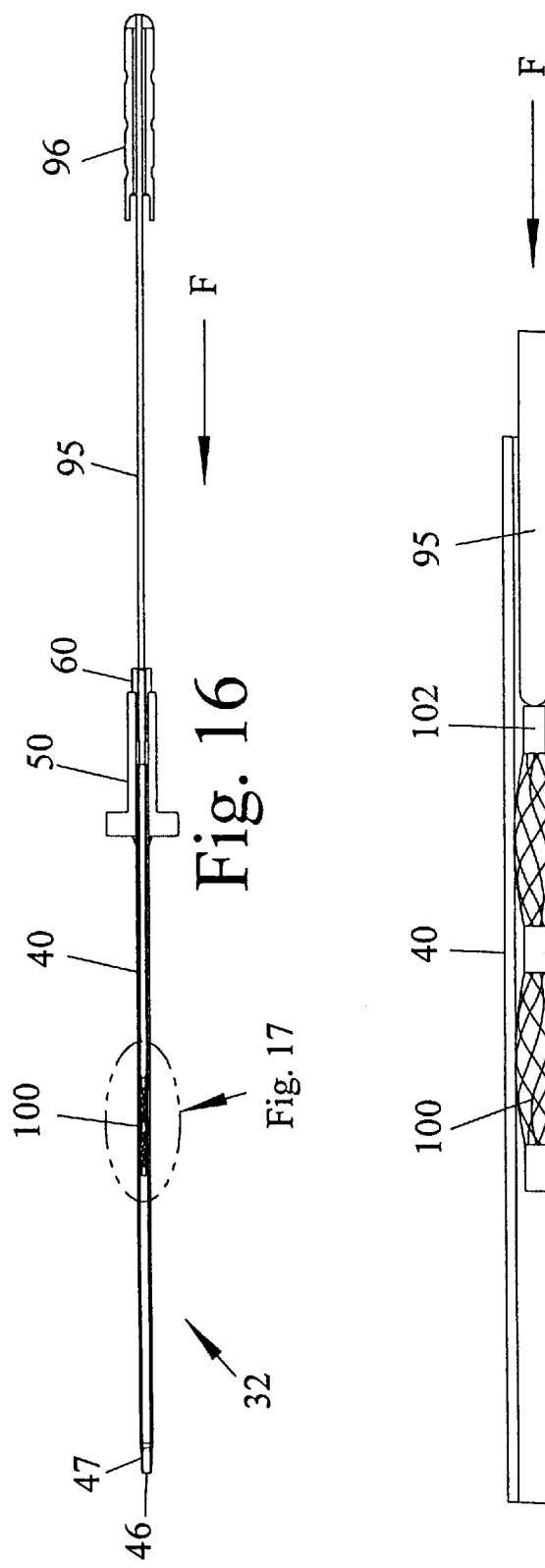

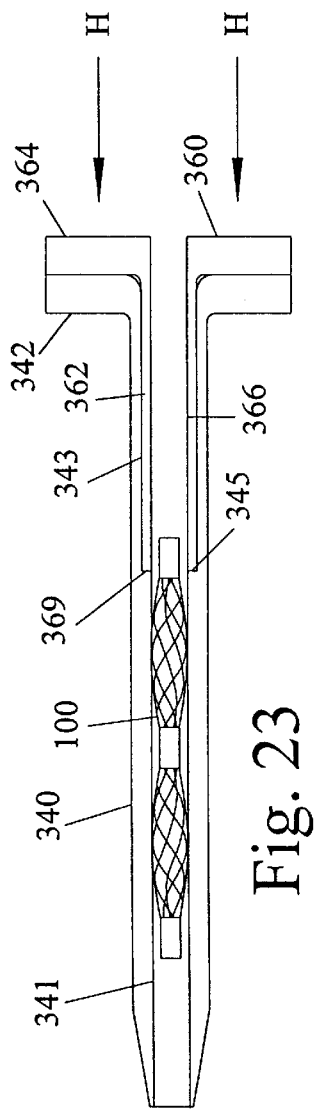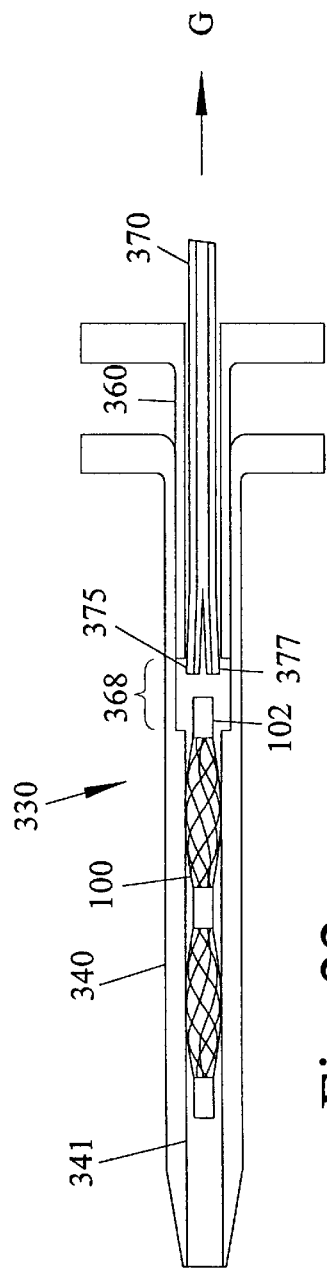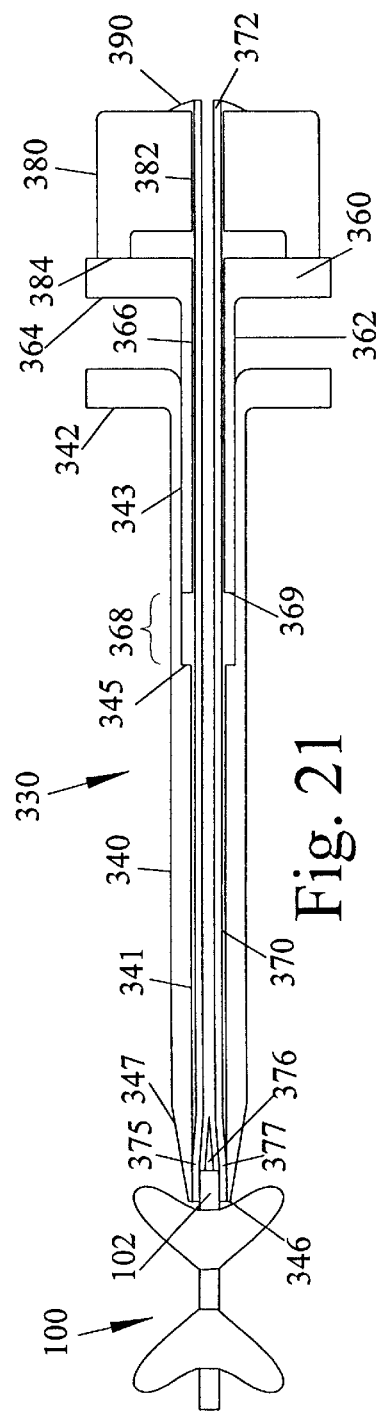

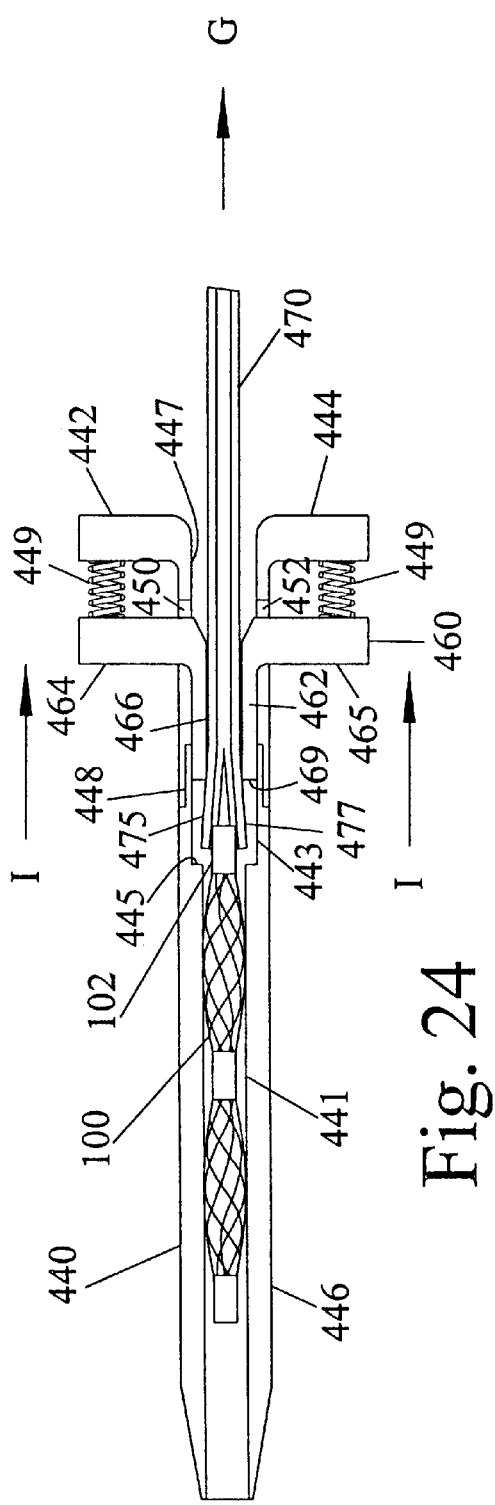
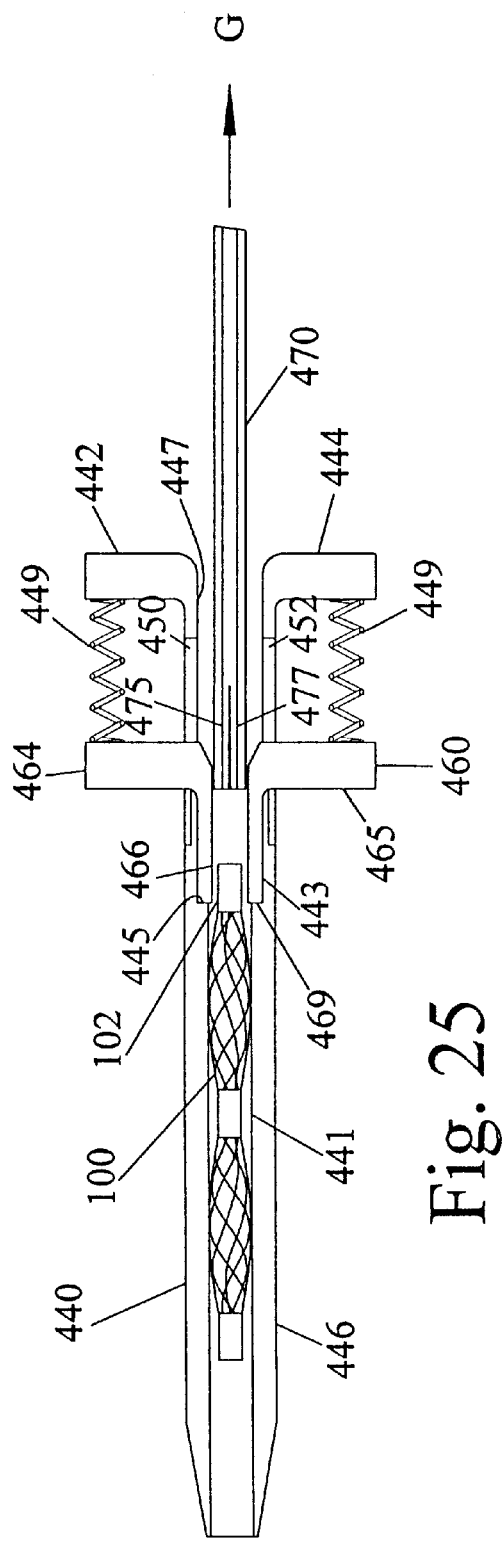
Fig. 24
Fig. 25

_5,984,944_

INTRODUCER FOR AN EXPANDABLE VASCULAR OCCLUSION DEVICE

CROSS-REFERENCE TO RELATED APPLICATIONS, IF ANY

This application is a continuation in part of U.S. patent application Ser. No. 08/927,535 filed Sep. 12, 1997, U.S. Pat. No. 5,895,410.

STATEMENT REGARDING FEDERALLY SPONSORED RESEARCH OR DEVELOPMENT

Not applicable.

REFERENCE TO A MICROFICHE APPENDIX, IF ANY

Not Applicable.

BACKGROUND OF THE INVENTION

1. Field of the Invention

The present invention relates, generally to medical devices. More particularly, the invention relates to expandable implantable devices, particularly vaso-occlusion devices used in radiology and embolotherapy. Specifically the invention relates to devices and methods for installing vaso-occlusion devices.

2. Background Information

In embolotherapy, it is often desirable to occlude blood flow in a section of vasculature for purposes such as controlling internal bleeding, stopping blood supply to tumors, and relieving vessel-wall pressure in a region of a vessel aneurysm. Several devices and methods have been developed for such purposes, many of which are described in U.S. Pat. No. 4,994,069. Each has significant drawbacks, but the helical wire coils seem to have found the most favor. One difficulty with helical wire coils is in pushing, and, if necessary, pulling them through the catheter. The wire coil is dimensioned to engage the walls of a blood vessel and can be relatively stiff and difficult to advance through a catheter, especially if the blood vessel has a tortuous path. U.S. Pat. Nos. 5, 226,911 and 5,250,071 describe mechanical devices that attach and detach to the coils to provide more positive pushing, pulling and positioning capability, but they are relatively complex.

The device of U.S. Pat. No. 4,994,069 (the '069 patent) overcomes many of the problems with wire coils. It provides a smaller coiled wire that when tensioned has a linear configuration allowing it to be advanced through a catheter to the desired site. When the wire exits the catheter, it relaxes and takes a random convoluted shape to form a space-filling mass lodged in the vessel at the site of release. However, because the final shape of the relaxed coil in the blood vessel is random, the precise location and specific length the device occupies in the vessel cannot be guaranteed. Straightening the long coiled wire and inserting it into a catheter can also be problematic.

A device which overcomes the problems associated with the device of the '069 patent is described in a pending U.S. patent application, Ser. No. 08/608,110, titled Self-Expanding Vascular Occlusion Device, filed on Feb. 28, 1996. The above application is hereby incorporated by reference.

The present invention provides a device and method of loading an expandable vascular occlusion device of the Ser. No. 08/608,110 application into a catheter for insertion into vasculature of a patient. A device and method of the present invention may also be useful to load other expandable devices into catheters, including the device of the '069 patent and other wire coils.

Expandable implantable devices which could benefit from the present invention include any device which has a stretched condition characterized by an elongated shape of smaller diameter and a relaxed condition characterized by a shorter shape of larger diameter. In the past, such expandable devices have been stored in their stretched condition inside a tube. The device may experience creep during long term storage in that condition. Such creep may prevent the device from fully returning to the intended shape in its relaxed condition. This is especially a problem with devices using plastic material in their springy components. Another potential problem with devices stored in a tubes is that such storage prevents a physician or anyone else from examining the device before it is installed. The storage tube may have a label with a picture or illustration of the device and a description. There is always a potential for mislabeling the tube, or even for the device to be missing from the tube.

An introducer of the present invention allows an expandable implantable device to be attached to the tip of the introducer, but the device remains in its relaxed condition outside of the introducer. The device is not subject to creep during long term storage in this condition, and the device can be examined to verify the device is appropriate for the intended use before the package containing the device and introducer is opened.

It is an object of the present invention to provide an introducer for use with an expandable implantable device which holds the device in its relaxed condition outside of the introducer.

It is another object of the present invention to provide an introducer for use with an expandable implantable device which pulls the device into the introducer, moving it into its stretched condition as it does so.

It is yet another object of the invention to provide an introducer for use with an expandable implantable device which places the device in its stretched condition in a predetermined position within the introducer.

BRIEF SUMMARY OF THE INVENTION

The present invention provides an apparatus for introducing a self expanding vascular occlusion device or other expandable implantable device into a catheter. The invention comprises an outer tube and an inner core sliding within an axial bore in the outer tube. The inner core has a distal end, a distal end portion of tubular configuration with at least one slot which allows the distal end portion to expand radially to receive and grip an end of an implantable device. The inner core has a proximal end extending beyond the proximal end of the outer tube when the distal end of the inner core is aligned with the distal end of the outer tube. The expandable implantable device is held by an introducer of the present invention in its relaxed condition outside of the outer tube prior to use.

An expandable implantable device is attached to an introducer of the present invention by first positioning the inner core relative to the outer tube so that the distal end portion of the inner core extends beyond the distal end of the outer tube. An end of an expandable implantable device is inserted into the distal end of the inner core so that the distal end portion expands radially and grips the end of the device. The inner core is slid proximally to move the distal end portion gripping the end of the implantable device into the outer tube's axial bore at its distal end, thereby tightening the grip of the distal end portion on the end of the implantable device. Proximal motion of inner core is stopped when the distal end of the inner core is aligned with the distal end of said outer tube. A handle may then be attached to the proximal end of the inner core, the handle being constructed and arranged to interact with the proximal end of the outer tube so as to prevent said inner core from sliding distally and releasing the end of the implantable device.

To use an introducer of the present invention, the inner core is slid proximally which pulls the expandable device into the axial bore of the outer tube tightening the inner core's grip on the end of the device and moving the device to its stretched condition as it does so. Continued sliding of the inner core proximally moves the implantable device along the axial bore of the outer tube. When the distal end of the inner core exits the proximal end of the outer tube, the distal end portion releases the implantable device such that most of the device remains disposed inside the outer tube in its stretched condition. The distal end of the outer tube is then installed in an opening in a catheter and a pushrod is used to push the device in its stretched condition distally back along the axial bore of the outer tube and into the catheter.

In one embodiment, the introducer further includes a hub having an axial bore which receives the outer tube. The hub has a larger diameter portion to facilitate manual gripping. The proximal end of the hub aligns with the proximal end of the inner tube.

In another embodiment a similar hub is used. This hub extends proximally beyond the proximal end of said outer tube, and a sleeve is mounted in the axial bore of the hub at the proximal end of the hub. The sleeve has an axial bore with a diameter matching that of the outer tube. The distal end of the sleeve is disposed within the axial bore of the hub and spaced a distance from the proximal end of the outer tube. This gap between the sleeve and the outer tube is sufficiently large to allow the distal portion of said inner core to release the implantable device as the distal end of the inner core exits the proximal end of the outer tube.

In another embodiment the outer tube has a stepped inner bore with a larger diameter portion at the proximal end, a smaller diameter portion at the distal end, and a shoulder where the two portions meet. A slidable sleeve is selectively positionable along the proximal portion of the axial bore such that the distal end of the sleeve is spaced a distance from the shoulder or the distal end of said sleeve abuts the shoulder. The slidable sleeve has an axial bore the same diameter as the distal portion of the axial bore of the outer tube. When the sleeve is spaced a distance from the shoulder, the implantable device is released from the inner core when the distal end of the inner core passes the shoulder. After the inner core is removed, the sleeve can be slid distally so that the distal end of the sleeve butts against the shoulder thereby closing the gap along the bore. This facilitates use of a push rod having a flexible tip which may miss the implantable device or buckle while trying to push the device back through the outer tube.

In another similar embodiment a slidable sleeve is spring loaded to keep the gap closed until the distal end portion of the inner core holding the end of the implantable device pushed it open. To facilitate this, the axial bore of the sliding sleeve has a slightly smaller diameter than that of the distal portion of the outer tube, but the diameter is still large enough to allow the inner core to slide smoothly in it. After the implantable device is released from the inner core, the distal end portion of the inner core contracts and slides through the bore of the sleeve and the springs then push the sleeve distally until the gap is again closed.

All of these embodiments may have a handle attached to the proximal end of the inner core after the implantable device is attached to facilitate manual grasping of the inner core and to prevent said inner core from sliding distally and releasing the end of the implantable device.

The features, benefits and objects of this invention will become clear to those skilled in the art by reference to the following description, claims and drawings.

BRIEF DESCRIPTION OF THE SEVERAL VIEWS OF THE DRAWING

FIG. 1 is an isometric view of one embodiment of the introducer of the present invention as used with a self expanding vascular occlusion device.

FIG. 2 is a partially exploded cross sectional view taken along the line 2—2 of FIG. 1.

FIG. 3 is an exploded view of the delivery portion of the delivery portion 32 of the embodiment of FIG. 1.

FIG. 4 is a partially exploded view of the embodiment of FIG. 1 as seen during assembly.

FIG. 5 is an enlarged view of the area indicated in FIG. 4.

FIG. 6 is a cross sectional view taken along the line 6—6 of FIG. 1.

FIG. 7 is an isometric view of the embodiment of FIG. 1 as seen during assembly with a self expanding vascular occlusion device exploded away from the introducer.

FIG. 8 is an isometric view of the embodiment of FIG. 1 as seen during assembly with a self expanding vascular occlusion device attached from the introducer.

FIG. 9 is an enlarged view of the area indicated in FIG. 8.

FIG. 10 is an enlarged view of the area indicated in FIG. 1.

FIG. 11 is a partial cross sectional view along line 11—11 of FIG. 9.

FIG. 12 is a cross sectional view of the distal end of the embodiment of FIG. 1 as used with a wire coil vascular occlusion device.

FIG. 13 is the view of FIG. 11 with a self expanding vascular occlusion device partially retracted into the introducer.

FIG. 14 is an enlarged view of FIG. 6 showing how a self expanding vascular occlusion device is released from the retracting portion as the retracting portion is retracted.

FIG. 15 is the view of FIG. 14 with the retracting portion removed.

FIG. 16 is a cross sectional view of the embodiment of FIG. 1 and a pushing device which may be used to push an expandable implantable device out of the delivery tube.

FIG. 17 is an enlarged view of the area indicated in FIG. 16.

FIG. 18 is a cross sectional view of the distal tip of the embodiment shown in FIG. 16 with the introduced installed in a catheter and a self expanding vascular occlusion device being pushed from the introducer into the catheter.

FIG. 21 is a cross sectional view of a fourth embodiment of the introducer of the present invention with a self expanding vascular occlusion device attached to it. This embodiment uses a slip sleeve.

FIG. 22 is the view of FIG. 21 showing the self expanding vascular occlusion device being retracted into it.

FIG. 23 is the view of FIG. 22 with the retracting portion removed showing how he slip sleeve closes.

FIG. 24 is a cross sectional view of a fifth embodiment of the introducer of the present invention with a self expanding vascular occlusion device retracted into it. This embodiment uses a spring loaded sliding sleeve.

FIG. 25 is the view of FIG. 24 after the device has been released.

DETAILED DESCRIPTION

Figure 19:
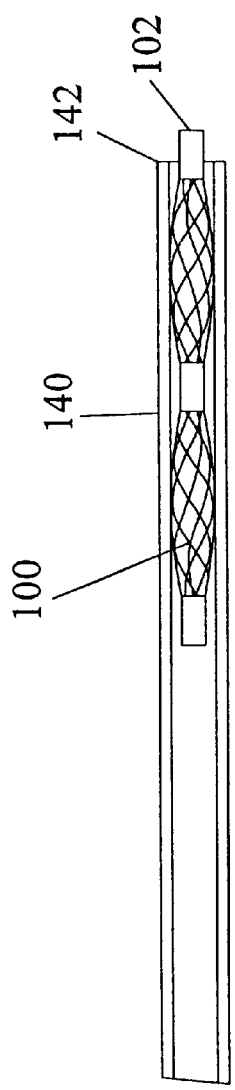
FIG. 19 is a cross sectional view of the proximal end of a delivery portion of a second embodiment of the introducer of the present invention with a self expanding vascular occlusion device retracted into it.

Referring to FIGS. 1–15, an example of one embodiment of the present invention is illustrated and generally indicated by the reference numeral 30. The introducer 30 is described below first in terms of its major structural elements and then in terms of its secondary structural and/or functional elements which cooperate to perform the introducing function.

Referring to FIGS. 1 and 2, introducer 30 comprises an outer tubular delivery portion 32 and an inner core portion 34 which slides inside delivery portion 32. Inner core 34 has a handle 80 attached to facilitate manual grasping of it. Inner core 34 has distal end portion 74 which is tubular and is longitudinally slit to grip an end of an expandable implantable device 100 and hold it at tip 46 of delivery portion 32 until device 100 is to be used. At that time inner core 34 is manually pulled proximally, in the direction indicated by arrow A, which pulls expandable device 100 into delivery portion 32 collapsing device 100 as it does so. As inner core 34 is pulled through delivery portion 32, device 100 is pulled proximally inside of delivery portion 32 until distal end portion 74 of inner core 34 reaches gap 68 in delivery portion 32 whereat slit distal end portion 74 expands to release device 100. Inner core 34 is then removed from delivery portion 32. Device 100 is then introduced into a catheter by inserting tip 46 of delivery portion into a catheter and pushing device 100 back through delivery portion 32 using an appropriate diameter pushrod.

Referring to FIGS. 2 and 3, outer delivery portion 32 comprises a delivery tube 40, a hub 50, and a sleeve 60. Delivery tube 40 and sleeve 60 are mounted in hub 50 so that a gap 68 of length L1 is left between de livery tube 40 and sleeve 60. Hub 50 has a cylindrical shank 52 having, a proximal end 54 and a distal end 56. In this embodiment, shank 54 has a larger diameter portion at distal end 56 to facilitate manual gripping as delivery portion 32 and retracting portion 34 are pulled relative to each other. An axial bore 58 extends all the way through hub 50 from proximal end 54 to distal end 56.

Delivery tube 40 has a proximal end portion 42 and a distal end portion 44. Proximal end portion 42 is inserted into bore 58 at distal end 56 of hub 50 until a point 48 on delivery tube 40 aligns with distal end 56 of hub 50. Delivery tube 40 is then bonded in place with adhesive 92, such as epoxy. Distal end portion 44 of delivery tube 40 has an exterior taper 47 to tip 46.

Sleeve 60 is a tubular body having a distal portion 62 and a proximal portion 64. Sleeve 60 has an inner diameter which matches that of delivery tube 40. Distal portion 62 of sleeve 60 has an outer diameter which also matches that of delivery tube 40. Proximal portion 64 has an outer diameter larger than that of distal portion 62 but smaller than the outer diameter of shank 52 of hub 50. Shoulder 66 is formed at the juncture of distal portion 62 and proximal portion 64. Distal portion 62 of sleeve 60 is inserted into bore 58 at proximal end 54 of hub 50 until shoulder 66 stops against proximal end 54 of hub 50 and sleeve 60 is bonded in place. The lengths of hub 50, proximal end portion 42 of delivery tube 40 and distal portion 62 of sleeve 60 are such that a gap 68 is left between delivery tube 40 and sleeve 60 when they are properly bonded in bore 58 of hub 50. This gap is important to facilitate releasing of an expandable device by retracting portion 34 and care must be taken that material used to bond delivery tube 40 and sleeve 60 into hub 50 does not flow into gap 68.

Referring to FIGS. 2, 4, and 5, inner core 34 comprises a collet tube 70 and handle 80. Collet tube 70 has a proximal end portion 72 and a distal end portion 74. Collet tube 70 is preferably tubular throughout its length, but it mat be a solid core with only its distal end portion being tubular. Distal end portion 74 has a longitudinal slit 76 bifurcating it for a length of L2 into portions 75 and 77. After delivery portion 32 has been assembled, proximal end portion 72 of collet tube 70 is inserted into tip 46 of delivery tube 40 and slid through delivery portion 32 in the direction indicated be arrow B so that proximal end portion 72 extends well beyond sleeve 60.

Referring to FIGS. 2, 4, and 6, handle 80 has an axial bore 82 of sufficient diameter to receive collet tube 70. At distal end 89 of handle 80, axial bore 82 has a portion 84 of sufficient diameter and length to receive sleeve 60 with a slight friction fit and allow distal end 89 of handle 80 to butt against proximal end 54 of hub 50. In this embodiment, portion 84 is larger diameter than the rest of axial bore 82, but all of axial bore 82 may have a diameter of portion 84. In this embodiment, handle 80 has external features such as circumferential grooves 86 to facilitate manual gripping of handle 80.

Handle 80 is slipped over proximal end portion 72 of collet tube 70, which extends beyond sleeve 60, and slid along collet tube 70 in the direction indicated by arrow C so that sleeve 60 engages portion 84 of axial bore 82 and distal end 89 of handle 80 butts against proximal end 54 of hub 50. Collet tube 70 is then further advanced through delivery portion 32 in the direction indicated by arrow B so that distal end portion 74 of collet tube 70 is near tip 46 of delivery tube 40 and proximal end portion 72 of collet tube 70 extends beyond proximal end 88 of handle 80.

Referring to FIGS. 7, 8, and 9, an expandable implantable device such as a vascular occlusion device 100, described in pending U.S. patent application, Ser. No. 08/608,110 is installed in distal end portion 74 of collet tube 70. Expandable vascular occlusion device 100 has a plurality of hubs 102 and a plurality of braided wires 104 connecting hubs 102. Braided wires 104 have been heat set so that when device 100 is in a relaxed state as shown in FIGS. 7, 8, and 9, device 100 resembles two cones with apexes pointing toward each other. For simplicity, only an outer contour of device 100 is illustrated. When hubs 102 are pulled axially, device 100 stretches into a tubular form of greater length and smaller diameter than it has in its relaxed state.

An end hub 102 of device 100 is inserted into distal end portion 74 of collet tube 70. The inside diameter of collet tube 70 is smaller than the outer diameter of hub 102. In one embodiment, hub 102 has an outer diameter of 0.030 inches and collet tube 70 has an inner diameter of 0.017 inches. The larger diameter of hub 102 forces slot 76 to open as hub 102 is advanced into distal end portion 74 thereby separating portions 75 and 77 of collet tube 70. Preferably, nearly the entire length of hub 102 is inserted into distal end portion 74. Length L2 of slot 76 should be long enough that hub 102 can be easily inserted, but short enough that portions 75 and 77 resist being separated and thereby grip hub 102. In this embodiment, slot length L2 is about twice the length of hub 102.

Referring to FIGS. 1, 10 and 11, with device 100 held by portions 75 and 77 of collet tube 70, collet tube 70 is than further advanced through delivery portion 32 so that portions 75 and 77 are withdrawn into delivery tube 40 and end 79 of collet tube 70 is approximately flush with tip 46 of delivery tube 40. Portions 75 and 77 should not be withdrawn so much into delivery tube 40 that wires 104 are deformed by tip 46 of delivery tube 40.

Referring to FIGS. 1 and 6, with device 100 properly positioned relative to delivery tube 40, adhesive 90 such as epoxy is applied to proximal end 88 of handle 80 and collet tube 70 at proximal end 88 of handle 80 to secure collet tube 70 to handle 80. After adhesive 90 has solidified, excess collet tube 70 extending beyond adhesive 90 is trimmed off. Introducer 30 with expandable implantable device 100 attached is now completed and ready to be stored. It may be sterilized and stored in a sealed transparent bag or tube.

Referring to FIG. 12, other expandable implantable devices such as vascular occlusion coil 110 may be used with introducer 30. An end 112 of coil 110 is inserted between portions 75 and 77 of collet tube 70 and withdrawn into tip 46 of delivery tube 40 in a similar manner as was hub 102 of device 100.

An introducer of the present invention may be suitable for use with any other expandable implantable device, such as a stent, which has a stretched condition characterized by an elongated shape of smaller diameter and a relaxed condition characterized by a shorter shape of larger diameter. An implantable device remains attached to the introducer but the device remains in its relaxed condition outside of the introducer. The device is not subject to creep during long term storage in this condition, and the device can be examined to verify the device is appropriate for the intended use before the package containing the device and introducer is opened.

Referring to FIGS. 1, 11 and 13, when an implantable device such as device 100, is to be introduce into a catheter, handle 80 is manually pulled away from hub 50 in the direction indicated be arrow A, which moves collet tube 70 in the direction indicated by arrow D and pulls expandable device 100 into delivery tube 40 collapsing device 100 as it does so.

Referring to FIG. 11, distal end portion 44 of delivery tube 40 has an inner wall portion 41 of reduced diameter extending from tip 46 to transition region 45 between inner wall portion 41 and inner wall 43. The diameter of inner wall portion 41 is reduced from the diameter of the inner wall 43 along the rest of delivery tube 40 to compensate for the reduced radial stiffness due to the tapering wall thickness in distal end portion 44. As hub 102 and portions 75 and 77 of collet tube 70 are drawn into distal end portion 44 of delivery tube 40, distal end portion 44 compresses portions 75 and 77 of collet tube 70 firmly against hub 120 like a collet. Portions 75 and 77 exert an outward force on distal portion 44. Because the wall thickness of distal portion 44 is thinner than the rest of delivery tube 40, distal portion 44 will deform outward more than the rest of delivery tube 40. If inner wall portion 41 had a diameter the same as inner wall 43 of the rest of delivery tube 40, the greater outward expansion near tip 46 may reduce the holding force of portions 75 and 77 against hub 102 enough that hub 102 would pull out of collet tube 70 as collet tube 70 is further retracted and frictional resistance of wires 104 against tip 46 is encountered. Such an occurrence would render introducer 30 useless. The reduced diameter of inner wall portion 41 compensates for that by forcing distal end portion 44 to elastically expand more than the rest of delivery tube 40 as portions 75 and 77, and hub 102 pass. A greater compression force is exerted on portions 75 and 77 than if the diameter of inner wall portion 41 had not been reduced. The compression load of the distal end portion 44 with a thinner wall of lesser inner diameter expanding farther is then similar to that of the rest of delivery tube 40 with a thicker wall of greater inner diameter expanding less. That maintains enough holding force on hub 102 so it does not pull out of collet tube 70 as device 100 is pulled into delivery tube 40.

In one embodiment, the inner diameter of reduced diameter portion 41 is 0.040 inches and the inner diameter of the rest of delivery tube 40 is 0.043 inches. The corresponding outer and inner diameters of collet tube 70 are 0.031 and 0.014 inches respectively. The outer diameter of hub 102 used with tubes of those dimensions is 0.030 inches, resulting in a 0.004 inch diametric compression.

Referring to FIG. 13, as device 100 is pulled into distal end portion 44 of delivery tube 40, braided wires 104 encounter tip 46 which forces wires 104 to collapse as device 100 is stretched and pulled. The half of device 100 inside delivery tube 40 has been stretched into a tubular shape tube with braided wires 104 oriented more as illustrated. Braided wires 104 bulge out against delivery tube 40 as much as allowed by the diameters of inner wall portions 41 and 43. In a similar fashion, the remaining portion of device 100 is pulled into distal end portion 44 of delivery tube 40.

Referring to FIG. 14, collet tube 70 and device 100 is retracted in a direction indicated by arrow E along delivery tube 40 until portions 75 and 77 of collet tube 70 reach gap 68 between delivery tube 40 and sleeve 60 in hub 50. As end 79 of collet tube emerges from delivery tube 40, portions 75 and 77 are no longer radially constrained by inner wall 43 of delivery tube 40 and they spring open releasing hub 102. Collet tube 70 is then pulled the remaining distance out through sleeve 60. Gap 68 has a length sufficient to allow portions 75 and 77 to release hub 102. That length is preferably at least as long as the length L2 of slot 76 between portions 75 and 77.

Referring to FIGS. 15, device 100 is now positioned in delivery tube 40 such that end hub 102 is partially protruding into gap 68. Friction between wires 104 and inner wall 43 keep device 100 in that position.

Referring to FIGS. 16, 17 and 18, to introduce device 100 into a catheter 120, external taper 47 of delivery tube 40 is inserted into an end 122 of catheter 120, which frictionally holds delivery tube 40 in place. Catheter 120 preferably has an inner diameter close to the inner diameter of delivery tube 40, however, it is not necessary to have a close diameter match. A catheter could be, for example, 0.007 inches larger. A pushrod 95 having an outer diameter similar to that of collet tube 70 is inserted into sleeve 60 and advanced distally in the direction indicated by arrow F until tip 97 contacts hub 102. Pushrod 95 may optionally have a handle 96 attached which is similar to handle 80 on collet tube 70. Pushrod 95 is then further advanced to push device 100 distally inside of delivery tube 40, out tip 46 of delivery tube 40 and into catheter 120. Delivery tube 40 may then optionally be removed from catheter 120 for further advancing of device 100 through catheter 120 with another pushrod or appropriately sized guidewire.

Referring to FIG. 15, sleeve 60 helps align a pushrod so it makes proper contact with hub 102 of device 100 when device 100 is to be pushed out of delivery tube 40. however sleeve 60 and even hub 50 are not necessary for an introducer of the present invention to function properly.

Referring to FIG. 19, one alternate embodiment is to use only a delivery tube 140 without a sleeve or hub. When a collet tube is retracted out proximal end 142 of delivery tube 140, hub 120 will be released leaving a portion of hub 120 protruding from proximal end 142. Device 100 can be pushed back into delivery tube 140 a little by pinching hub 120 between a person's thumb and forefinger and pushing it into delivery tube 140 resulting in hub 120 being approximately flush with proximal end 142 of delivery tube 140. A pushrod can then be applied to hub 120 and used to advance device in tube 140. While construction of this embodiment is simpler, the small outer diameter of delivery tube 140 may make it more difficult to hold when retracting a collet tube or inserting and pushing a pushrod.

Figure 20:
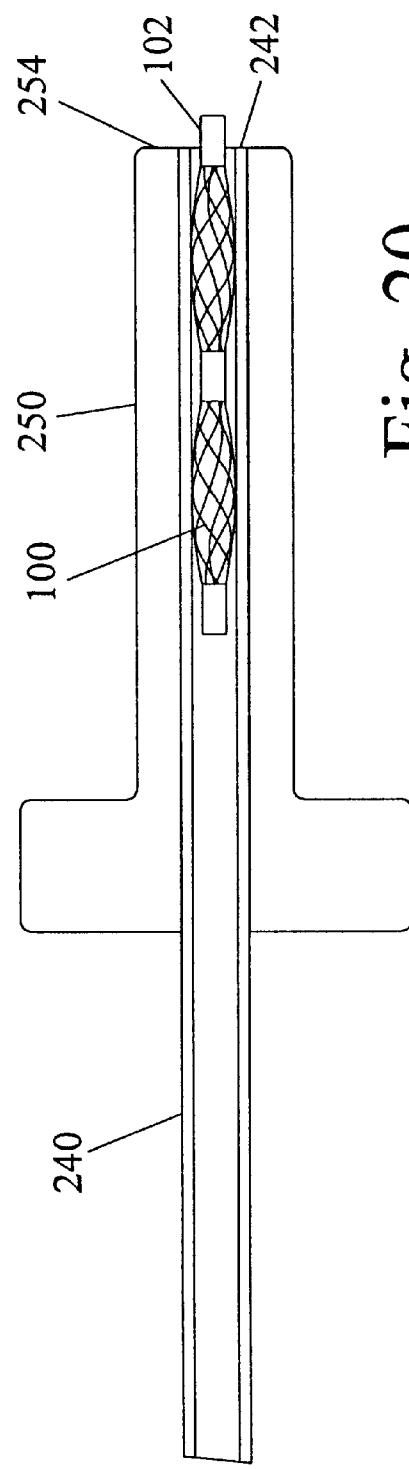
FIG. 20 is a cross sectional view of the proximal end of a delivery portion of a third embodiment of the introducer of the present invention with a self expanding vascular occlusion device retracted into it.

Referring to FIG. 20, another alternate embodiment shown works the same way as the embodiment of FIG. 15, but hub 250 attached to tube 240 provides a better grip on delivery tube 240 when retracting a collet tube or inserting and pushing a pushrod. Proximal end 254 of hub 25 is preferably flush with proximal end 242 of delivery tube 240.

Referring to FIGS. 21, 22 and 23, another embodiment of an introducer of the present invention is shown in longitudinal cross section. Introducer 330 has a delivery tube 340 which may be shorter than in previous embodiments. Delivery tube 340 has an axial bore with a distal portion 341 having the same diameter as the inner wall 43 of most of the delivery tube 40 of previous embodiment, and a proximal portion 343 having a diameter of axial bore 58 of hub 50 of a previous embodiment. A shoulder 345 is formed at the junction of portion 341 and 343. Axial bore proximal portion 343 receives slip sleeve 360. Delivery tube has a flange 342 at its proximal end and an external taper 347 at its distal end terminating in tip 346. Delivery tube 340 preferably may have a greater wall thickness than delivery tube 40 of previous embodiments and external taper 347 may be steeper than external taper 47 of previous embodiments. In that case it is not necessary that axial bore distal portion 341 have a reduced diameter corresponding to external taper 347.

Slip sleeve 360 has a flange 364 at its proximal end and a shank 362 extending distally from flange 364 which fits inside axial bore proximal portion 343 of delivery tube 340. Slip sleeve 360 is positioned in bore portion 343 to form gap 368 between shoulder 345 and distal end 369 of slip sleeve. The fit between shank 362 and bore portion 343 should be a snug sliding fit which is tight enough that gap 368 is maintained during normal handling of introducer 330 and retracing of collet tube 370, but loose enough that gap 368 can be closed by manually sliding slip sleeve distally by pushing on flange 364. Slip sleeve 360 has an axial bore 366 of the same diameter as axial bore distal portion 341 of delivery tube 340.

Collet tube 370 has the same dimensions, except for length, as collet tube 70 of previous embodiments. It has a proximal end 372 bonded to handle 380 and a slot 376 at its distal end which bifurcates it into portions 375 and 377 which hold hub 102 of device 100 at tip 346 of delivery tube 340.

Handle 380 has an axial bore 382 which receives proximal end 372 of collet tube 370, and a face 384 which abuts flange 364 when device 100 is properly held at tip 346. Adhesive 390 affixes handle 380 to collet tube 370.

Device 100 is drawn into delivery tube 340 in the same manner as with previous embodiments. Delivery tube 340 is held while handle 380 is pulled proximally in a direction indicated by arrow G, which pulls collet tube 370 distally and withdraws device 100 into axial bore distal portion 341 of delivery tube 340. As shown in FIG. 22, hub 102 of device 100 is released from collet tube 370 when portions 375 and 377 reach gap 368. Collet tube 370 is then removed from slip sleeve 360.

Referring to FIG. 23, slip sleeve 360 is then pushed in a direction indicated by arrow H so that shank 362 slides in axial bore proximal portion 343 of delivery tube 340 until distal end 369 of slip sleeve 360 abuts shoulder 345 of delivery tube 340 thereby closing gap 368. Flanges 342 and 364 are then adjacent each other. Axial bore distal portion 341 of delivery tube 340 and axial bore 366 of slip sleeve now form a bore having one uniform diameter throughout its length. This is important if a pushrod having a small diameter flexible tip is to be used to push device 100 out of delivery tube 340 and through a catheter. If gap 368 were left, the larger inner diameter at gap 368 may allow the flexible tip to miss hub 102 of device 100 or buckle while trying to push hub 120, thereby making it impossible to begin pushing device 100 out of delivery tube 340. Closing the gap 368 to make a smaller continuous diameter prevents those occurrences. Introducer 330 has an additional advantage of fewer parts and less assembly than the embodiment having the separate hub and sleeve which must be assembled. The length of gap 368 can also be adjusted if necessary. The relative position of flanges 364 and 342 provide a visual indicator of the length of gap 368.

Referring to FIG. 24, another embodiment of an introducer of the present invention uses a spring loaded sliding sleeve to close the gap. Introducer 430 has delivery tube 440 similar to delivery tube 340 of the previous embodiment in that the wall thickness, tip configuration, and dimensions of axial bore distal portion 441, proximal portion 443, and shoulder 445 are the same. Delivery tube 440 has a proximal portion 444 and a distal portion 446 joined together at joint 448. Joining may be done by bonding or by designing joint 446 to snap together. Proximal portion 444 has a flange 442 at its proximal end and an axial bore 447 of the same diameter as bore 443.

Slip sleeve 460 has a shank 462 which slides inside bores 443 and 447. Axial bore 466 of slip sleeve 460 is slightly smaller than the diameter of bore 441 of delivery tube 440, but still large enough that collet tube 470 will easily slide in it. Tabs 464 and 465 protrude in opposite directions through longitudinal slots 450 and 452 in proximal portion 444 of delivery tube 440. Springs 449 act between flange 442 and tabs 464 and 465 to keep slip sleeve 460 disposed distally in slots 450 and 452 such that distal end 469 of slip sleeve 460 abuts shoulder 445 of delivery tube 440. Collet tube 470 is identical to collet tube 370 of the previous embodiment and has a similar handle (not shown) attached.

As collet tube 70 retracts proximally in a direction indicated by arrow G and pulls device 100 into delivery tube 440, portions 475 and 477 reach distal end 469 of slip sleeve 460. Friction between portion 475 and 477 and 466 slip sleeve 460 caused slip sleeve to slide proximally in the direction indicated by arrows I. That motion continues until portions 475 and 477 clear shoulder 445 at which point hub 102 of device 100 is released from between portions 475 and 477.

Referring to FIG. 25, as collet tube continues to be retracted in the direction indicated by arrow G, portions 475 and 477 can come back together and slide out of bore 466 as collet tube 470 is removed. Springs 449 then push slip sleeve 460 distally until distal end 469 abuts shoulder 445 of delivery tube 440. Device 100 can then be pushed distally into a catheter. The components of all the above embodiments are preferably made of a thermoplastic material.

Figure 26:
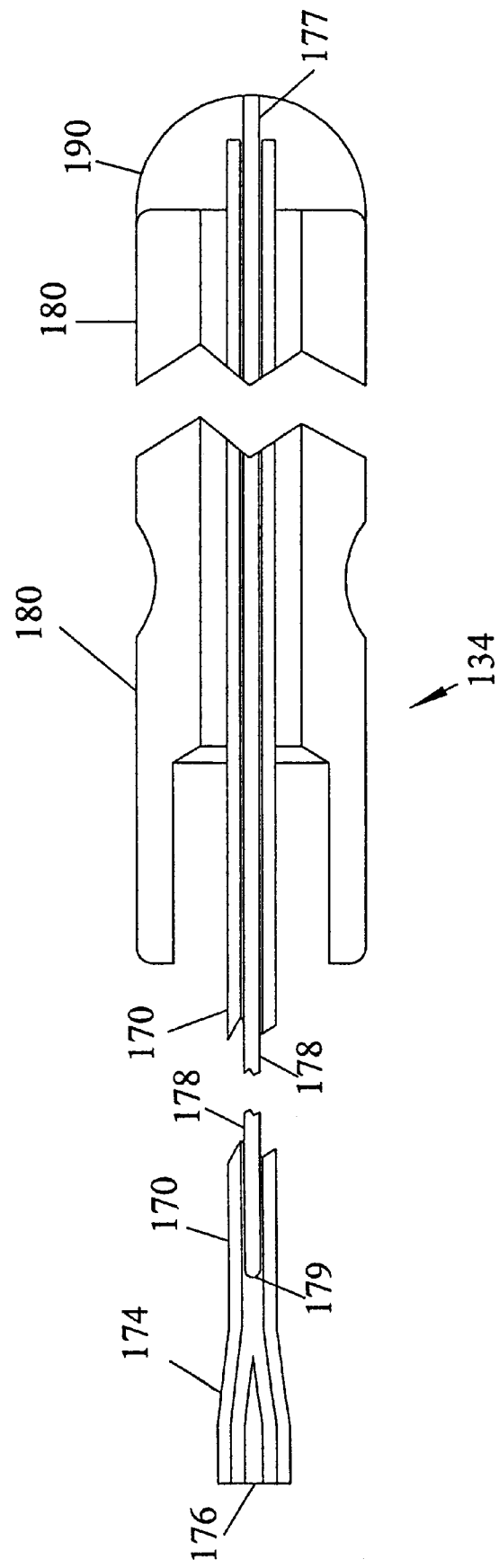
FIG. 26 is an alternate embodiment of the retractable portion of the device wherein the retractable portion has an internal metal rod.

Referring to FIG. 26, another embodiment of the inner core 34 which applies to all other embodiments above is inner core 134 having a metal wire 178 disposed inside collet tube 170. Metal wire 178 has a proximal end 177 embedded in adhesive 190 and extends distally along collet tube 170 until it terminates at a distal end 179, which is disposed proximally of slit 176 at distal end portion 174 of collet tube 170. Metal wire 178 provides something solid for collet tube 170 to cinch down against as collet tube elongates and shrinks diametrically under tensile load, thereby reducing recoil or "snapping" of collet tube 170 as the inner core 134 is pulled proximally to retract a device. Metal wire 178 has an outer diameter that is preferably about 0.002 inches less than the inner diameter of collet tube 170 to aid insertion of metal wire 178 into collet tube 170.

The embodiment shown in FIG. 26 may be used with implantable devices, such as stents, that have no solid hub for the slit distal end portion 174 of collet tube 170 to cinch against. In that case, distal end 179 of metal wire 178 may extend into slit 176 of distal end portion 174, or beyond collet tube 170 to provide a solid core against which a stent can be clamped by distal end portion 174 of collet tube 170.

Figure 27:
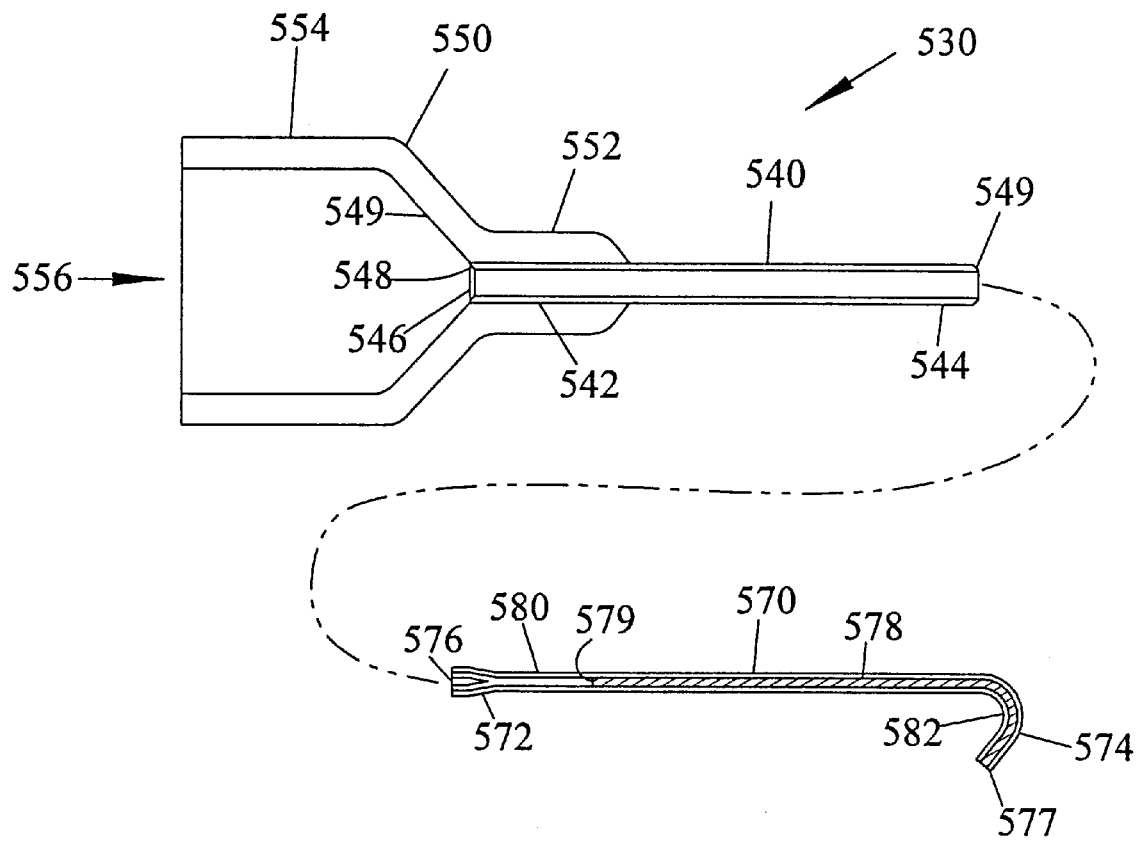
FIG. 27 is a cross sectional partially exploded view of a sixth embodiment of the introducer having a shield on one end.
Figure 28:
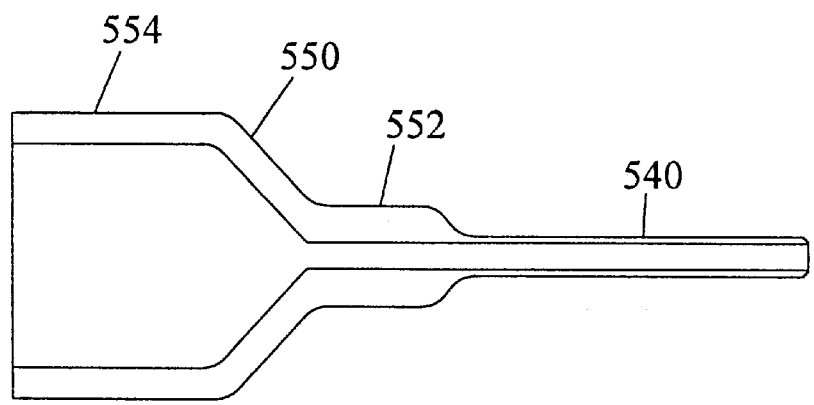
FIG. 28 is a cross sectional view of a unitarily molded embodiment of a portion of the introducer of FIG. 27.
Figure 29:
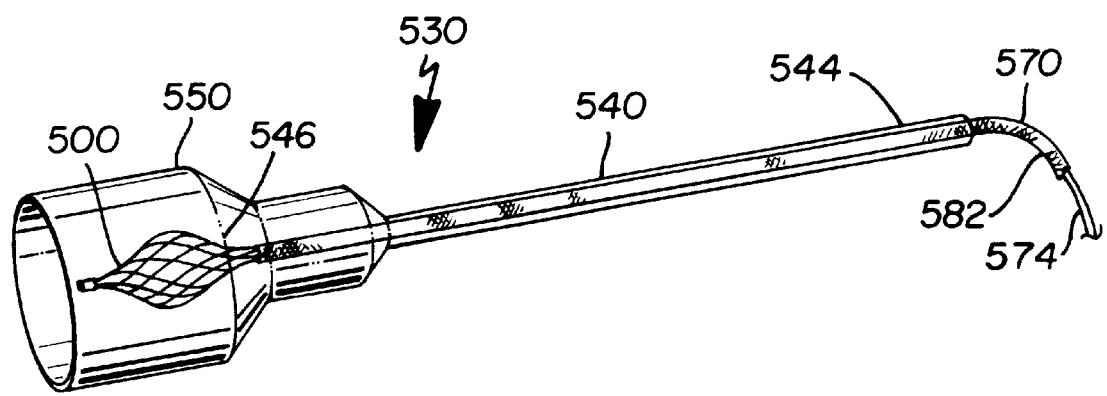
FIG. 29 is a perspective view of the introducer of FIG. 27 with a self expanding vascular occlusion device attached.

Referring to FIGS. 27–29, a sixth, embodiment of the introducer 530 is illustrated.

A delivery tube 540 has a cup-shaped transparent shield member 550 affixed to its first end portion 542. The shield member 550 protects device 500 and also facilitates introduction of a pusher or guidewire into the delivery tube 540 to push the device 500 into a catheter. Collet tube 570 holds a self expanding vascular occlusion device 500, which in this illustration is a ball-shaped device, in a relaxed condition at first end 546 of delivery tube 540 and within shield member 550. Second end portion 574 of collet tube 570 extending beyond second end 544 of delivery tube 540 is bent into a hook shape 582 to function as a handle and also to prevent the collet tube 570 from sliding back toward the shield member 550 and releasing device 500.

Shield member 550 is connected to a first end portion 542 of delivery tube 540. Shield member 550 preferably has a shank portion 552 with an internal bore which receives first end portion 542 of delivery tube 540. Shank portion 552 is affixed to delivery tube 540 by methods such as gluing or welding, or shank portion 552 may simply have a friction fit on delivery tube 540 and be pressed on it. Shield member 550 could also be molded directly onto delivery tube 540. Alternatively, as illustrated in FIG. 28, shield member 550 and delivery tube 540 could be molded as a single unit. In that case, delivery tube 540 could be an integrally molded extension of shank portion 552.

Shield member 550 also has cup portion 554 extending from shank portion 552. Cup portion 554 has an internal bore 556 large enough to receive a self expanding vascular occlusion device with generous clearance around the device. Bore 556 has a tapered portion 558 extending from end 546 of delivery tube 540. The tapered portion 548 guides a pusher or guidewire inserted into bore 556 into end 546 of delivery tube 540.

Delivery tube 540 is similar to delivery tube 40. It is preferably a rigid material such as metal or plastic. First end 546 of delivery tube 540 opens into bore 556 but does not extend into bore 556. First end 546 may have an internal chamfer 548 or radius to facilitate device 500 being pulled into delivery tube 540. Delivery tube 540 has a second end 544 which may have an external chamfer 549 or radius to facilitate it being inserted into a catheter.

Collet tube 570 is similar to the collet tube of FIG. 26 in that, in this embodiment, it has a metal wire 578 disposed inside of a flexible tube, preferably made of material such as polyethylene. The first end portion 572 of collet tube 570 has a longitudinal slit 576 which allows first end portion 572 to expand radially to receive and grip an end of device 500.

Metal wire 578 is coextensive with second end 577 of collet tube 570, and has an end 579 which terminates a significant distance from first end portion 572 of collet tube 570 leaving a portion 580 of collet tube 570 unreinforced by wire 578. Besides providing something solid for collet tube 570 to cinch down against, wire 578 also provides stiffness and memory to second end portion 574 of collet tube 570 so it can be shaped to facilitate grasping.

To install a device 500 in the introducer 530, second end 577 of collet tube 570 is inserted into first end 546 of delivery tube 540 and pushed through delivery tube 540 until second end portion 574 of collet tube 570 extends beyond second end 544 of delivery tube 540 and slit first end 572 of collet tube 570 extends an inch or so beyond shield member 550. An end of device 500 is installed in the slit first end 572 of collet tube 570, then second end portion 574 is pulled to slide collet tube 102 further through delivery tube 540 and pull device 500 inside of cup portion 554 of shield member 550. When the end 572 of collet tube 570 gripping the device 500 enters the first end 546 of delivery tube 540, the grip of end 572 of collet tube 570 on the end of device 500 is tightened by compressive loading of end 572 of collet tube 570. Sliding of collet tube 570 is then stopped. Second end portion 574 of collet tube 570 is then bent to form a hook 582 at second end 544 of delivery tube 540. The hook 582 serves as a handle for grasping collet tube 570 to retract device into delivery tube 540, and also functions to prevent the collet tube 570 from sliding back toward the shield member 550 and releasing device 500.

As shown in FIG. 29, device 500 is held by introducer 530 in its relaxed condition outside of the delivery tube 540 prior to use. To use the device and the introducer, the hook 582 of the collet tube 570 is grasped and pulled relative to delivery tube 540, which pulls device 500 into delivery tube 540 stretching device 500 to its cylindrical shape as it does so. Continued sliding of the collet tube 570 moves the device 500 along the delivery tube 540. When the first end 572 of the collet tube 570 exits second end 544 of the delivery tube 540, the collet tube 570 releases the device 500 such that most of the device remains in its stretched condition disposed inside the delivery tube 540 at second end 544. Collet tube 570 is discarded and second end 544 of the delivery tube 540 is installed in a catheter. A push rod is then inserted into first end 546 of delivery tube 540 and advanced until it contacts device 500. The pushrod is used to push the device in its stretched condition into the catheter and advance it through the catheter to the desired site of deployment. Shield member 550 provides a large diameter grasping member useful for manually holding the catheter while manipulating the pushrod.

Figure 30:
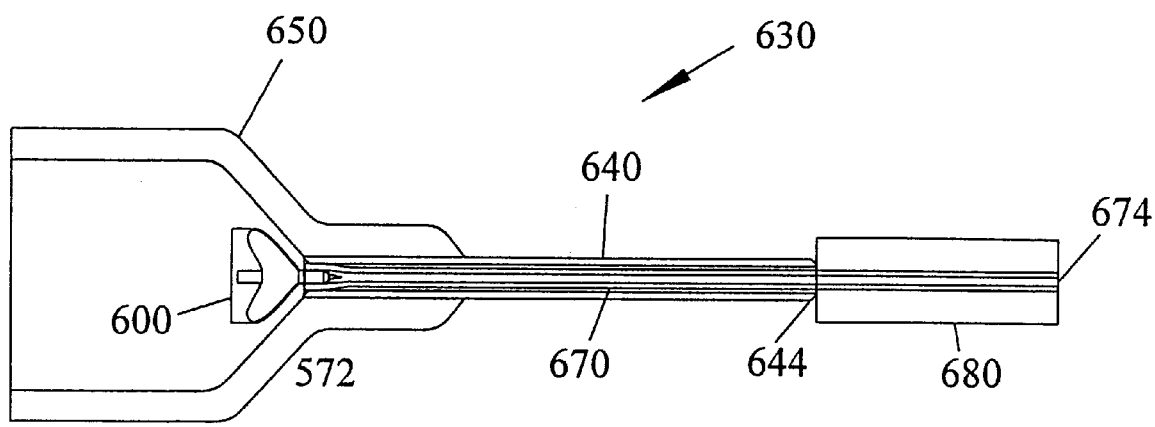
FIG. 30 is a cross sectional view of a seventh embodiment of the introducer with a self expanding vascular occlusion device attached.

A seventh, and most preferable, embodiment is illustrated in FIG. 30. The delivery tube 640 and shield member 650 of introducer 630 are the same as delivery tube 540 and shield member 550 in FIG. 27. The collet tube 670 is similar to collet tube 70 of FIG. 2 in that it does not have a metal wire inside of it, and it has a handle 680 attached at its end 674. If collet tube 670 is sufficiently thick and/or rigid, a metal wire is not needed inside of the collet tube. The introducer 630 is shown assembled and holding a conical shaped covered self expanding vascular occlusion device 600 in its relaxed state. The introducer 630 and device 600 are assembled using the same procedure described above for introducer 530 except that rather than bending the end of the collet tube, after sliding of collet tube 670 in delivery tube 640 is stopped, handle 680, which is a sleeve, is slid over collet tube 670 from end 674 until it reaches end 644 of delivery tube 670. Collet tube 670 and handle 680 are then unitized to prevent movement of collet tube 670 in the opposite direction. Any excess collet tubing extending beyond handle 680 is trimmed.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

What is claimed is:

1. An introducer for introducing an implantable device into a catheter, comprising:
   (a) a delivery tube having a first end, a first end portion, a second end and an axial bore which receives an inner core, the delivery tube further comprising a shield member connected to the first end portion of the delivery tube, the shield member having a cavity sufficiently large to receive the implantable device in a relaxed condition, the cavity communicating with the axial bore of the delivery tube; and
   (b) the inner core slidably disposed inside the axial bore of the delivery tube, the inner core having a first end, a first end portion of tubular configuration with at least one slot which allows the first end portion to expand radially to receive and grip the end of an implantable device, the inner core having a second end portion extending beyond the second end of the delivery tube when the first end of the inner core is aligned with the first end of the delivery tube, the inner core sliding through the axial bore of the delivery tube to pull an implantable device into the axial bore of the delivery tube, the first end portion of the inner core releasing the implantable device when the first end of the inner core exits the second end of the delivery tube such that most of the implantable device remains disposed inside the delivery tube.

2. The introducer of claim 1, wherein the delivery tube has a first end portion having an external taper.

3. The introducer of claim 2, wherein the axial bore of the delivery tube has a second portion of greater diameter and a first portion of lesser diameter, the first portion being adjacent the external taper.

4. The introducer of claim 1, further comprising a handle connected to the second end portion of the inner core.

5. The introducer of claim 1, further comprising a wire disposed inside the inner core.

6. The introducer of claim 5, wherein the wire has a first end disposed a substantial distance from the at least one slot.

7. The introducer of claim 5, wherein the inner core has a second end, and the wire has a second end disposed at the second end of the inner core.

8. The introducer of claim 5, wherein the inner core is tubular having an inner diameter, and the wire has an outer diameter that is less than the inner diameter of the tubular inner core.

9. The introducer of claim 1 further comprising a hub connected to the delivery tube, the hub having an axial bore which receives the delivery tube, a first end, a first portion of larger outer diameter, a second portion of smaller outer diameter, and a second end; the delivery tube being received in the axial bore of the hub and the delivery tube extending beyond the first end of the hub.

10. The introducer of claim 9, wherein the second end of the delivery tube aligns with the second end of the hub.

11. The introducer of claim 10, further comprising a handle connected to the second end of the inner core, the handle being disposed adjacent the hub when the first end of the inner core is aligned with the first end of the delivery tube.

12. The introducer of claim 9, wherein the second end of the hub extends beyond the second end of the delivery tube.

13. The introducer of claim 11, further comprising a sleeve received by the axial bore of the hub at the second end of the hub, the sleeve having a first end, a second end and an axial bore, the axial bore of the sleeve receiving the inner core, the first end of the sleeve being disposed within the axial bore of the hub and spaced a distance from the second end of the delivery tube, the distance being sufficiently long to allow the first portion of the inner core to release the implantable device as the first end of the inner core exits the second end of the delivery tube.

14. The introducer of claim 13, wherein the axial bore of the sleeve and the axial bore of the delivery tube are the same diameter.

15. The introducer of claim 13, wherein the second end of the sleeve extends beyond the second end of the hub.

16. The introducer of claim 15, further comprising a handle connected to the second end of the inner core, the handle having a recess which receives the second end of the sleeve, the handle being disposed adjacent the hub when the first end of the inner core is aligned with the first end of the delivery tube.

17. The introducer of claim 2, wherein
   (a) the delivery tube has a flange on the second end;
   (b) the axial bore of the delivery tube has a second portion of greater diameter which receives a sleeve, a first portion of lesser diameter which receives the inner core, and a shoulder where the second portion meets the first portion; and further comprising:

(c) a sleeve slidably engaging the second portion of the axial bore of the delivery tube, the sleeve having an axial bore which receives the inner core, a first end, a second end, a flange at the second end, a shank extending from the flange and into the second portion of the axial bore of the delivery tube, the sleeve being selectively positionable along the second portion of the axial bore of the delivery tube such that (1) the first end of the sleeve is spaced a distance from the shoulder or (2) the first end of the sleeve abuts the shoulder, and when the sleeve is spaced a distance from the shoulder, the implantable device is released from the inner core when the first end of the inner core passes the shoulder.

18. The introducer of claim 17, wherein the shank of the sleeve has a length such that a distance between the flange on the delivery tube and the flange on the sleeve is the same as the distance between the shoulder in the delivery tube and the first end of the sleeve.

19. The introducer of claim 18, wherein the axial bore of the sleeve and the first portion of the axial bore of the delivery tube are the same diameter.

20. The introducer of claim 18, further comprising a handle attached to the inner core such that the handle is adjacent the flange on the sleeve when the first end of the inner core is aligned with the first end of the delivery tube and the sleeve is positioned so that the first end of the sleeve is spaced from the shoulder in the delivery tube.

21. The introducer of claim 17 wherein the sleeve is spring loaded against the flange of the delivery tube to normally keep the first end of the sleeve butted against the shoulder, but when the first end portion of the inner core gripping an end of an implantable device reaches the first end of the sleeve, the sleeve moves with the first end portion of the inner core until the first end of the inner core passes the shoulder and releases the implantable device, whereupon the first portion of the inner core contracts radially and the sleeve slides over the first end portion of the inner core until the first end of the sleeve once again butts against the shoulder.

22. The introducer of claim 1, wherein the shield member is substantially transparent.

23. The introducer of claim 1, further comprising a handle disposed on and attached to the second end portion of the inner core and adjacent the second end of the delivery tube when the first end of the inner core is aligned with the first end of the delivery tube.

24. An introducer for introducing an implantable device into a catheter, comprising:

(a) a delivery tube having a first end, a second end and an axial bore which receives an inner core; and (b) an inner core slidably disposed inside the axial bore of the delivery tube, the inner core having a first end, a first end portion of tubular configuration with at least one slot which allows the first end portion to expand radially to receive and grip the end of an implantable device, the inner core having a second end portion extending beyond the second end of the delivery tube when the first end of the inner core is aligned with the first end of the delivery tube, the second end portion of the inner core being bent, the inner core sliding through the axial bore of the delivery tube to pull an implantable device into the axial bore of the delivery tube, the first end portion of the inner core releasing the implantable device when the first end of the inner core exits the second end of the delivery tube such that most of the implantable device remains disposed inside the delivery tube.

25. An introducer for introducing an implantable device into a catheter, comprising:

(a) a delivery tube having a first end, a second end and an axial bore which receives an inner core; and (b) an inner core slidably disposed inside the axial bore of the delivery tube and a wire disposed inside the inner core, the inner core having a first end, a first end portion of tubular configuration with at least one slot which allows the first end portion to expand radially to receive and grip the end of an implantable device, the inner core having a second end and the wire having a second end disposed at the second end of the inner core, the inner core having a second end portion extending beyond the second end of the delivery tube when the first end of the inner core is aligned with the first end of the delivery tube, the second end portion of the inner core being bent, the inner core sliding through the axial bore of the delivery tube to pull an implantable device into the axial bore of the delivery tube, the first end portion of the inner core releasing the implantable device when the first end of the inner core exits the second end of the delivery tube such that most of the implantable device remains disposed inside the delivery tube.

26. The introducer of claim 25, wherein the second end portion of the inner core is bent in the shape of a hook.

27. A system for providing an expandable implantable device for introduction into a catheter comprising:

(a) an expandable implantable device having an end, a relaxed condition of a predetermined diameter and a predetermined length, and a stretched condition of lesser diameter and longer length; and (b) an introducer for introducing the expandable implantable device into a catheter, the introducer having:

(i) a delivery tube having a first end, a first end portion, a second end and an axial bore which receives an inner core, the delivery tube further comprising a shield member connected to the first end portion of the delivery tube, the shield member having a cavity sufficiently large to receive the implantable device in a relaxed condition, the cavity communicating with the axial bore of the delivery tube;

(ii) an inner core slidably disposed inside the axial bore of the delivery tube, the inner core having a first end, a first end portion constructed to receive and grip the end of the implantable device, the end of the expandable device disposed in and gripped by the first end portion of the inner core, the first end portion with the end of the implantable device disposed in the axial bore of the delivery tube at the first end of the delivery tube so that the implantable device remains in the relaxed condition and most of the implantable device is outside of the delivery tube, the inner core being slidable to thereby pull the expandable device into and along the axial bore of the delivery tube in the stretched condition and to release the implantable device from the first end portion when the first end of the inner core exits the second end of the delivery tube such that most of the implantable device remains in the stretched condition and disposed inside the delivery tube.

28. The system of claim 27, wherein the inner core has a second end extending beyond the second end of the delivery tube, and further comprising a handle attached to the second end of the inner core, the handle constructed and arranged to interact with the delivery tube so as to prevent the inner core from sliding in a direction which would release the end of the implantable device.

29. The system of claim 27, wherein the implantable device is a self expanding vascular occlusion device.

30. The system of claim 27, wherein the implantable device is a wire coil for occluding vasculature.

31. An introducer for introducing an implantable device into a catheter, comprising:
   (a) a delivery tube having a first end, a first end portion having an external taper, a second end and an axial bore which receives an inner core, the axial bore having a second portion of greater diameter and a first portion of lesser diameter, the first portion being adjacent the external taper;
   (b) a hub connected to the delivery tube, the hub having an axial bore which receives the delivery tube, a first end, a first portion of larger outer diameter, a second portion of smaller outer diameter, and a second end, the delivery tube being received in the axial bore of the hub and the delivery tube extending beyond the first end of the hub, the second end of the hub extending beyond the second end of the delivery tube;
   (c) a sleeve received by the axial bore of the hub at the second end of the hub, the sleeve having a first end, a second end and an axial bore, the axial bore of the sleeve receiving an inner core, the first end of the sleeve being disposed within the axial bore of the hub and spaced a distance from the second end of the delivery tube, the second end of the sleeve extending beyond the second end of the hub;
   (d) an inner core slidably disposed inside the axial bore of the delivery tube and the axial bore of the sleeve, the inner core having a first end, a first end portion of tubular configuration with at least one slot which allows the first end portion to expand radially to receive and grip an end of an implantable device, the inner core having a second end portion extending beyond the second end of the delivery tube when the first end of the inner core is aligned with the first end of the delivery tube, the second end portion of the inner core being bent, the inner core sliding through the axial bore of the delivery tube to pull an implantable device into the axial bore of the delivery tube, the first end portion of the inner core releasing the implantable device when the first end of the inner core exits the second end of the delivery tube such that most of the implantable device remains disposed inside the delivery tube; and
   (e) a handle connected to the second end of the inner core, the handle having a recess which receives the second end of the sleeve, the handle being disposed adjacent the hub when the first end of the inner core is aligned with the first end of the delivery tube.

32. An introducer for introducing an implantable device into a catheter, comprising:
   (a) a delivery tube having a first end, a first end portion, a second end and an axial bore which receives an inner core;
   (b) a shield member connected to the first end portion of the delivery tube, the shield member having a cavity sufficiently large to receive the implantable device in a relaxed condition, the cavity communicating with the axial bore of the delivery tube;
   (c) a tubular inner core slidably disposed inside the axial bore of the delivery tube, the inner core having a first end, a first end portion with at least one slot which allows the first end portion to expand radially to receive and grip an end of an implantable device, the inner core having a second end, and a second end portion extending beyond the second end of the delivery tube when the first end of the inner core is aligned with the first end of the delivery tube; and
   (d) a handle attached to the second end of the inner core, the handle constructed and arranged to interact with the delivery tube so as to prevent the inner core from sliding in a direction which would release the end of the implantable device; the inner core sliding through the axial bore of the delivery tube to pull the implantable device into the axial bore of the delivery tube, the first end portion of the inner core releasing the implantable device when the first end of the inner core exits the second end of the delivery tube such that most of the implantable device remains disposed inside the delivery tube.

33. A method of assembling an introducer of claim 1 with an expandable implantable device comprising the steps of:
   (a) positioning the inner core relative to the delivery tube so that the first end portion of the inner core extends beyond the first end of the delivery tube;
   (b) placing the implantable device into the cavity of the shield member proximate to the first end portion of the inner core;
   (c) inserting an end of an expandable implantable device into the first end of the inner core so that the first end portion expands radially and grips the end of the expandable implantable device;
   (d) sliding the inner core to move the first end portion with the end of the implantable device into the axial bore of the delivery tube at the first end of the delivery tube thereby tightening the grip of the first end portion on the end of the implantable device; and
   (e) stopping the sliding of the inner core when the first end of the inner core is aligned with the first end of the delivery tube thereby leaving the implantable device in a relaxed condition outside of the delivery tube.

34. A method of using a system of claim 27 comprising the steps of:
   (a) sliding the inner core to pull the expandable device from the cavity of the shield member and into the axial bore of the delivery tube, the expandable device thereby being moved to the stretched condition;
   (b) continuing to slide the inner core, thereby moving the implantable device along the axial bore of the inner core in the stretched condition, the first end portion of the inner core releasing the implantable device when the first end of the inner core exits the second end of the delivery tube such that most of the implantable device remains in the stretched condition and disposed inside the delivery tube;
   (c) inserting an end of the delivery tube into an opening in a catheter; and
   (d) inserting a pushrod into the delivery tube and advancing the pushrod to push the implantable device out the delivery tube and into the catheter, the implantable device remaining in the stretched condition.

* * * * *